United States Patent [19]
Pettit

[11] Patent Number: 5,821,536
[45] Date of Patent: Oct. 13, 1998

[54] SOLID STATE INFRARED GAUGE

[76] Inventor: John W. Pettit, 7808 Potters Mill Ct., Rockville, Md. 20855-1025

[21] Appl. No.: 978,133

[22] Filed: Nov. 25, 1997

Related U.S. Application Data

[63] Continuation of Ser. No. 474,122, Jun. 7, 1995.

[51] Int. Cl.[6] ............................ G01N 21/35; G01N 21/86
[52] U.S. Cl. .................. 250/339.1; 250/339.12; 250/358.1; 250/359.1
[58] Field of Search ............................ 250/341.7, 339.07, 250/339.08, 339.1, 339.12, 358.1, 359.1

[56] References Cited

U.S. PATENT DOCUMENTS

| | | | |
|---|---|---|---|
| 3,793,524 | 2/1974 | Howarth . | |
| 4,733,078 | 3/1988 | Sturm | 250/339.1 |
| 5,039,855 | 8/1991 | Kemeny et al. | 250/339.07 |
| 5,049,216 | 9/1991 | Shead et al. | 250/339.11 X |
| 5,120,961 | 6/1992 | Levin et al. | 250/339.07 |

OTHER PUBLICATIONS

"Acousto–optic Tunable Filters Spectrally Modulate Light", by X. Wang, *Laser Focus World*, (May 1992).

*Primary Examiner*—Edward J. Glick
*Attorney, Agent, or Firm*—Wigman, Cohen, Leitner & Myers, PC

[57] ABSTRACT

A solid state moisture gauge is disclosed in which a quartz-halogen bulb is used with an acousto-optic tunable filter to launch light of specific desired wavelengths into a parallel plate cavity device which contains or is adjacent to material having a moisture content which is to be measured. The light exiting from the parallel plate device is detected, converted to a digital signal and then stored in a computer for later comparison to the detection of light exiting from the parallel plate device of a different wavelength.

22 Claims, 5 Drawing Sheets

SOLID STATE INFRARED GAUGE

This is a continuation of co-pending application Ser. No. 08/474,122, filed on Jun. 7, 1995.

BACKGROUND OF THE INVENTION

The present invention is directed to an apparatus for measuring a characteristic of a web material. Particularly, the present invention is directed to an apparatus for measuring the moisture content or other near-infrared detectible characteristic of a web material.

The measurement of water or moisture in materials is a frequently needed capability in many aspects of manufacturing and for many products sold or distributed throughout the world. That is because water is the most frequently added or extracted material in the manufacturing process. The cost of excess water in manufactured articles is therefore significant. In many products, such as fabrics, it represents a weight that is undesired or that is non-productive and which must be paid for by the end user. In addition, the weight of the water adds to the cost of transportation and storage of the product. Often, excessive moisture is responsible for degrading the shelf-life of products.

Water is also rather expensive to remove from a product. It is therefore very desirable to measure and control the amount of water that initially goes into a product. Also, drying technology is inefficient, costly and can often degrade a product if, for example, heat, infrared radiation or dry air is used to effect the drying. Those are only some of the many factors that make it desirable to measure or control moisture in industrial processes.

It is a well-known technique that the moisture measuring technology utilize the near-infrared absorption of light by water molecules as the basic approach for a moisture analyzer. Infrared, being the wavelength region just beyond the visible light portion of the spectrum, is a region where molecules can readily absorb light at certain wavelengths characteristic to the molecule. These absorption peaks correspond to resonances formed by the bonds between the atoms within the water molecule. The set of wavelengths at which a molecule will absorb provides a signature in the infrared spectrum for that molecule that is created by the unique set of bonds which comprise that molecule.

It is well-known that water absorbs near-infrared light at wavelengths of 1.45 microns and 1.94 microns. The 1.94 micron wavelength is generally used in industrial applications because it uniquely identifies water molecules, since that resonance absorption is caused by the water molecules' H—O—H vibrational mode of excitation. The 1.45 micron absorption is due to the O—H bond and is therefore seen in many organic molecules.

In order to implement a moisture measurement apparatus using near-infrared radiation, the various wavelengths must be passed through the sample material to be measured and then separately analyzed by the instrument. A reference wavelength that is not sensitive to the presence of water must be measured as well as the characteristic wavelength. That is because infrared radiation is produced by any matter that has a temperature and, thus, there is a large background of infrared radiation present and therefore it is not reliable to simply measure the absorption of water at one wavelength. When measuring water, the reference wavelength is usually 1.7 microns. This is a very standard technique and is discussed, for example, in U.S. Pat. No. 3,793,524, which issued to Measurex Corporation on Feb. 19, 1974.

In order to generate or select the various wavelengths needed, prior art systems utilize fixed optical interference filters. Those are formed by the deposition of several layers of dielectric material on a glass substrate that are a fraction of the wavelength of the desired wavelength of the filter. In order to sequentially select the various wavelengths, those fixed filters are alternately placed into and taken out of the optical path of the instrument by means of a mechanical rotating wheel. Such wheels have a plurality of such filters and are driven by a motor with a servo-controlled system that is integrated with the measuring instrument itself. Such electro-mechanical systems form the heart of prior art moisture measuring instruments. Unfortunately, such mechanical rotating wheel-based systems are costly, complex, prone to errors from abuse, misalignment or shock, and are inflexible.

In order to make an analysis of water content, several wavelengths of light need to be evaluated and the optical filters are repeatedly moved into and out of the optical path. A synchronizing mark on the wheel is used to gate the electronics used to determine which filter is in action at each point in time. The electronics measures the light intensity transmitted through each filter as it passes through the optical beam and computes the moisture content of the sample. In order to correct for all background light, the light shining through the spinning wheel must also be turned off and on, usually by means of a mechanical shutter, in order to obtain a total background reading.

In order to overcome the shortcomings of the prior art mechanical wheel-type moisture gauges, tunable filters that work on the principle that sound waves launched into a material can diffract light that is also passing through the material in a process that is called Bragg diffraction have been proposed for use in their place. Such filters are termed acousto-optic tunable filters or AOTFs. The sound wave launched into the material can be thought of as periodic compressions and refractions of the material through which they travel. That causes a modulation of the index of refraction of the material for the light because the index of refraction is related to the density of the material.

All light entering the crystal will be defracted by the effective phase grating caused by the sound wave. However, only one wavelength of light can be made to be cumulatively diffracted and exit the crystal at a definite angle relative to the rest of the incoming light. That wavelength of light is related to the frequency of the sound wave in the crystal for which certain wave matching conditions are met. Thus, for each sound wave frequency generated, there is a unique optical wavelength that satisfies those conditions and is cumulatively diffracted. By selecting for analysis only the light that has exited the crystal at that angle, an optical filter is implemented.

The AOTF uses anisotropic Bragg diffraction in a crystal that is birefringent. That rotates the polarization of the diffracted light because the ordinary and extraordinary rays of the light do not see the same index of refraction and will therefore have different phase velocities. By carefully designing the physical layout of the filter, the acoustic wave can be made to propagate such that the group velocity for both the diffracted light and the incident light is the same. That is termed noncritical phase matching and gives the filter a workable field of view.

There are two general forms of AOTFs. These are collinear and non-collinear. In the apparatus of the present invention, a non-collinear configuration based on $TeO_2$ is utilized. In the apparatus of the present invention the two polarizations of the incident light exit the crystal at equal but opposite angles relative to the incident light. While there are many properties of the crystal that factor into its use for an AOTF, TeO$_2$ is preferable for its high acousto-optic figure of merit and because of the fact that it operates efficiently in the near-infrared spectrum up to about 4.5 microns.

The sound wave is launched into the crystal by means of a piezoelectric transducer that is mechanically bonded to one face of the crystal. An acoustic absorbing material is located on the other face of the crystal for acoustic impedance matching. That transducer is driven by a radio frequency signal preferably having about ½ to 1 watt of power. The frequency range of the radio frequency signal is about 20 MHz to 50 MHz. Those frequencies are generated by a digital synthesizer, which consists of a phase locked loop and a reference frequency source. The digital synthesizer is controlled by a microprocessor or digital divider circuit.

An example of a commercially available acousto-optic tunable filter is the near-IR acoustic-optic tunable filter, versions 1 and 2, which is available from Crystal Technology, Inc., of Palo Alto, Calif. The use of an AOTF for near-infrared spectrometry is generally shown in an article entitled Acousto-Optic Tunable Filters Spectrally Modulated Light, by X. Wang, published in the May 1992 edition of *Laser Focus World*.

By utilizing an AOTF to generate infrared radiation at certain specified wavelengths and passing that wavelength through material whose moisture content is to be determined, the apparatus of the present invention is able to eliminate the spinning filter wheel and its accompanying mechanical light chopper. Since water has a strong resonance absorption for infrared radiation at 1.94 microns and does not absorb much, if at all, at 1.7 microns, taking the ratio of the transmission of the infrared radiation of those two wavelengths gives a value that is found to be linearly related to the water content of the sample. The ratio of those two wavelengths is used, as briefly eluded to above, so that background reflection, non-resonant absorption due to the mass of the sample and other effects are cancelled out.

As previously described, in the prior art devices that utilize parallel plate infrared optics, a light source is placed on one side of the parallel plate optics device. It is accompanied by a tuning fork light chopper and a reflector and heat shield. As practiced in the prior art, all of the frequencies the light bulb emits are launched into the cavity in the parallel plate optics through an entrance hole. The light is mechanically chopped so that reference values of the light level can be obtained after detection of light exiting from the parallel plate optics, since background light which needs to be cancelled is always present.

As discussed, for example, in the Measurex patent, U.S. Pat. No. 3,793,524, the light launched into the cavity bounces around and through the material to be measured and multiply reflects, and then ultimately exits through an exit hole that is usually on the other side of the parallel plates from the light source. However, the Measurex patent also teaches that the exit hole can be on the same side. The Measurex patent teaches that the entrance and exit holes need to be offset from one another so that the light is forced to multiply reflect and pass through the material being measured before it is detected. It may therefore be detected on the same side of the web as it entered, if desirable.

When the light exits the parallel plate infrared optics, the various wavelengths are detected individually, usually by means of fixed interference filters. Two methods are typically utilized to accomplish that detection. The first is the use of a spinning filter wheel with a plurality of fixed filters. A second approach is the use of a beam splitter which makes the light go into two or more paths. Each path then has its own light filter and detector.

The present invention, while utilizing the features of the parallel plate infrared optics, launches into the parallel plate optics only the specific desired wavelengths of light that are to be used for detection, and not the complete spectrum from the light bulb. The light launched into the parallel plate optics may be electronically modulated, or turned on or off, so that it can be detected in a phase locked loop scheme in order to obtain greater signal-to-noise ratio performance. The single detector is then used to detect the light energy that is emitted from the exit hole.

The approach of the present invention is superior to the prior art because the beam splitter approach suffers from the fact that multiple detectors must be used. The use of multiple detectors is disadvantageous because each detector is prone to drift individually from the others. In addition, the use of multiple detectors is costly. The disadvantages of the spinning filter wheel approach have been set out in detail above.

SUMMARY AND OBJECTS OF THE INVENTION

In light of the foregoing shortcomings of the prior art moisture measurement devices, it is believed that there still exists a need in the art for a fully solid state moisture gauge which is small, compact, has no moving parts, does not produce vibrations and is rugged and not susceptible to movement or vibration.

It is, therefore, an object of the present invention to provide a solid state moisture gauge which can provide an on-line moisture measurement in industrial settings in an inexpensive and reliable manner.

The present invention utilizes a combination of a quartz-halogen bulb with a heat shield, an acousto-optic tunable filter and the components that drive or operate the AOTF, such as the RF amplifier, the digital synthesizer and the microprocessor or fixed control logic, as a light source generator that generates light of specific desired wavelengths. It will be understood by those of ordinary skill in the art that any devices for generating light at specific wavelengths can be used to launch the light into the parallel plate cavity device and the inventive apparatus would work just as well.

A single detector is then used to detect the light exiting from the parallel plate cavity device through the exit hole. The signal from the detector is amplified by the amplifier, converted to a digital signal by the analog-to-digital converter and then stored as a digital signal in the microprocessor or fixed control logic. As such, the instant invention has better performance than prior art devices, has solid-state reliability, no moving parts and is less expensive and more compact to produce.

DETAILED DESCRIPTION OF THE PREFERRED EMBODIMENT

Figure 1:
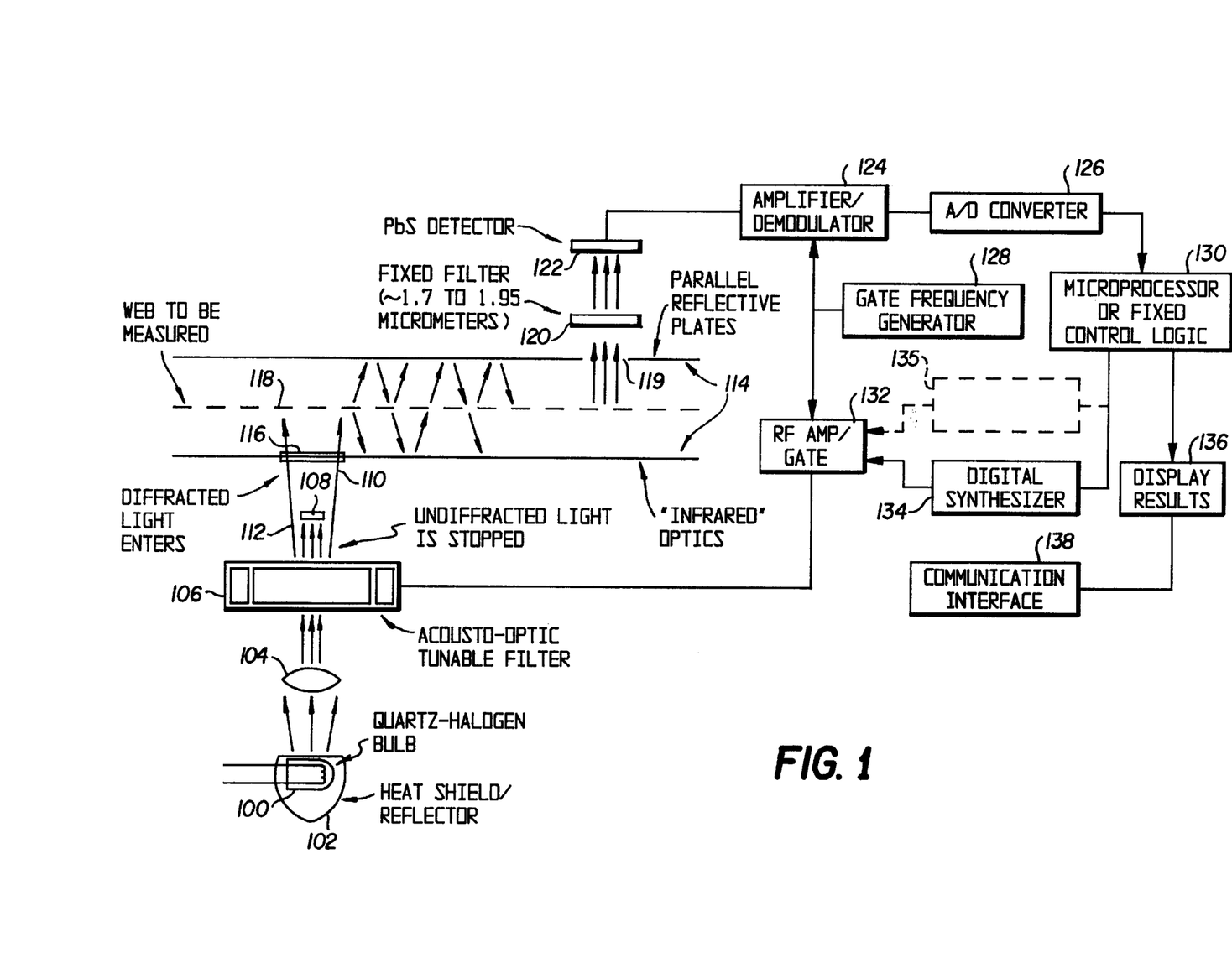
FIG. 1 is a schematic block diagram of the apparatus of the present invention.

Referring now to the drawings wherein like reference numerals are used to represent like elements throughout, there is shown in FIG. 1 a first embodiment of the apparatus of the instant solid state moisture gauge. As shown in FIG. 1, a multi-wavelength light source, such as a quartz-halogen bulb 100 with its associated heat shield/reflector 102 is utilized in conjunction with a lens 104 to impinge light onto an acousto-optic tunable filter 106. As will be described later herein, the acousto-optic tunable filter 106 is operated to generate selected wavelengths of infrared light, as discussed above, and to launch those light rays into the parallel plate optics 114 to form the light source that is referred to in the patent to Measurex Corporation.

The selected light rays at the desired wavelength exit the acousto-optic tunable filter 106 at angles relative to the unselected light from the light source 100. There are two light rays that are diffracted at equal but opposite angles from the rest of the light that passes straight through the acousto-optic filter 106. Those are the two polarizations of the diffracted light. Since polarization is not a concern for the inventive method and apparatus for measuring moisture or water, either or both of those rays 110, 112 are useful with the present invention. Preferably, the straight through light that is undiffracted and that consists of all of the undesired wavelengths of light produced by the quartz-halogen bulb light source 100 is blocked by the blocking device 108 positioned at the opposite side of the acousto-optic tunable filter 106 such that only the two desired diffracted rays 110, 112 exiting from the acousto-optic tunable filter 106 enter the parallel plate optics 114 through the entrance or aperture 116. In that manner, only light of the desired wavelength enters the parallel plate optics 114.

As previously discussed, it is also important to turn the light produced by the parallel plate optics on and off in order to obtain background readings to make an accurate measurement of the moisture contained in the web or other material 118 to be measured. Measuring the background rays is necessary in the infrared spectrum because of the amount of background radiation present, since all objects that are not at absolute zero temperature give off infrared radiation. In order to cancel out this unavoidable source of background radiation, the light source 100 would typically be turned on and off. In the prior art, that function was accomplished by a mechanical blocking mechanism that was attached to, for example, a tuning fork, which modulated the light on and off at the vibrational frequency of the tuning fork.

In the present invention, no mechanical device for turning the light on and off is utilized. Rather, the acousto-optic tunable filter 106 is utilized to achieve the background radiation cancellation as well. The radio frequency drive signal supplied to the acousto-optic tunable filter 106 is electronically modulated instead by the use of gate frequency generator 128 and gate 132. That generates the on and off rate of the frequency generator 128 for the phase locked detection. Due to the nature of the acousto-optic tunable filter 106, that modulation is also placed only on the desired wavelength of light, i.e., the light which enters the entrance or aperture 116. That light enters the parallel plate optics 114 with the modulation placed on it. All other light, whether such light is leakage from the AOTF filter 106 or ambient light that enters the parallel plate optics 114, will not have that modulation placed on it.

Since the modulation has been created electronically, the modulation drive signal can also be fed into a demodulator circuit 124 which is connected to receive the output of a lead sulfide (PbS) detector 122 or any suitable detector in order to implement a phase locked detection method for measuring the diffracted light. Thus, the apparatus of the present invention serves to increase the signal-to-noise ratio of the moisture measurement while at the same time eliminating the mechanical shutter system used in the prior art.

Phase locked detection methods are well-known in the art and will not be described further herein. However, such systems are well-known in many cases to provide increased signal-to-noise ratios by orders of magnitude. The present invention thus utilizes a phase—locked detection method in which the modulated and diffracted light from the acousto-optic tunable filter 106 is launched into the parallel plate optics 114 and the detected light exiting from an exit hole 119 in the parallel plate optics 114 is synchronously demodulated by means of the modulating signal to obtain the resultant measurement signal.

By utilizing the phase locked detection of the diffracted light described above, it is not necessary that the undiffracted light be blocked by the blocking mechanism 108 from entering the parallel plate optics 114. That is because the undesired, undiffracted light will not have the modulation placed on it and the phase locked detection will reject it in favor of the desired, diffracted light. Obviously, the desired diffracted light has the modulation placed on it and is accepted by the detector 122. Prior to impinging upon the detector 122, the light exiting from the exit hole 119 passes through an optional fixed interference filter 120 placed between the exit hole 119 and the detector 122. The fixed interference filter 120, when present, serves to block out any unnecessary light from reaching the detector 122.

The lead sulfide detector 122 is used to detect the light that exits at one or both diffraction angles from the AOTF 106. While only light from one of the diffracted angles from the acousto-optic tunable filter 106 need be allowed to enter the entrance hole 116 of the parallel plate optics 114 for the instant solid state moisture gauge to operate, the use of light from both diffraction angles provides for greater optical efficiency.

The moisture gauge of FIG. 1 operates as follows. The digital word is selected and output through a digital output port of a microprocessor or fixed logic control circuitry 130 to the digitally controlled radio frequency synthesizer 134. That word commands the digital synthesizer 134 to generate the proper radio frequency to cause the acousto-optic tunable filter 106 to select and diffract infrared light at a wavelength of 1.7 microns. The selected wavelength of infrared light 110, 112 generated by the acousto-optic tunable filter 106 as the result of the command from the digital synthesizer 134 is launched into the parallel plate optics 114 through the entrance hole 116 and passes multiple times through the sample 118 being measured. The diffracted wavelength of light 110, 112 then passes out through the exit aperture 119 and the optional fixed filter 120 to impinge on the detector 122.

The amplifier/demodulator 124 is connected to receive the signal generated by the impingement of the infrared light on the detector 122. It detects and amplifies the light at 1.7 microns in wavelength and rejects to a substantial degree all other light falling on the detector 122. The output from the amplifier/demodulator 124 is fed to an analog-to-digital converter 126 which converts the measurement of the light at a wavelength of 1.7 microns to a digital signal which is then input to the microprocessor 130 where it is stored in memory for later processing.

The microprocessor 130 next selects a digital word that will generate the proper radio frequency that will cause the acousto-optic tunable filter 106 to diffract light at 1.94 microns in wavelength. In the same manner as described above, the AOTF 106 generates and launches the light at 1.94 microns in wavelength into the parallel plate optics 114, where it again passes multiply through the sample 118, exits through the exit aperture 119 and falls onto the detector 122. In the same manner as discussed above in connection with the light at 1.7 microns in wavelength, the amplifier/demodulator 124 detects and amplifies the signal generated by the detector 122 as a result of the light at 1.94 microns in wavelength falling on it and the A–D converter 126 digitizes the amplified signal from the amplifier/demodulator 124, thus allowing the microprocessor 130 to input the result digitally into its memory for storage and later processing.

The microprocessor 130 then commands the digital synthesizer 134 to turn off completely so that no light is diffracted by the acousto-optic tunable filter 106. It should be noted, however, that this step is optional when the phase locked detection is utilized. However, without the phase locked detection scheme described above, this step is necessary to obtain the background light reading.

Assuming the phase locked detection scheme is not utilized, then the analog-to-digital converter 126 digitizes the background light reading impinging on the detector 122, and the microprocessor 130 then inputs the background reading digitally for storage and later processing. The microprocessor 130 then subtracts the digitized background reading from both of the digitized signals obtained at wavelengths of 1.7 microns and 1.94 microns.

The microprocessor 130 then computes the ratio of the readings at wavelengths of 1.7 microns and 1.94 microns. That ratio is linearly related to the moisture content of the sample. The ratio thus obtained by the microprocessor 130 is converted to a moisture reading in desired units by the formula:

$$\text{Moisture} = A * R + \text{Constant}, \tag{1}$$

where Moisture is the moisture content of the sample 118 in desired units, A is the proportional constant in a linear relation which is often termed the slope, Ratio is the measured ratio obtained in the above steps and Constant is the constant term in a linear relationship. The parameters A and Constant are calibration constants, since they are determined in separate calibration steps using samples of material with a known moisture content in a known manner.

The moisture value computed by the microprocessor 130 is then output to a display device 136 so that operators may view the moisture content of the sample. Alternatively, it may be output through a communications interface 138 for input to other devices to which the moisture gauge of the present invention is connected in a total system.

The above-described parameters A and Constant are determined by using calibration standards of known moisture contents and obtaining values of Ratio determined in steps as given above. Then, a linear regression is used to derive those parameters from the Ratios obtained from the set of known moisture standards in any manner that is well known in the art to obtain parameters of a straight line from sets of data.

Another way to measure moisture that is made possible by implementing a spectrometer in the manner discussed above, is to fit a curve to the water spectrum measured with a sample in place. A curve fitted to the data over the wavelength range of about 1.6 microns to 2.1 microns yields a measurement of the strength of the absorption. The area of the absorption peak can then be determined by integrating the fitted curve. That would utilize the many data points produced by the instant apparatus, rather than just taking a single sample at a point at the central place on the absorption line. The result would be greater accuracy in measurement of the moisture content of the sample 118.

In addition, another benefit of such an approach would be that the software described above could be enhanced to detect the presence of any material that might have an infrared absorption near the water or absorption region of 1.94 microns or near the baseline region of 1.7 microns. When that happens with prior art instruments, errors in measurement occur, which is a problem which is not easily solved. Usually, additional reference points are implemented with extra fixed filters in order to try to avoid the offending signature. With the apparatus of the present invention, however, software could be used that would examine the shape of the spectrum to make sure that it resembles the curves shown in, for example, FIGS. 5 and 6. If offending substances are present, then extra absorption lines, or bumps in the curve, will be seen and detected by the software.

When that happens, it is usually the baseline that becomes inaccurate, since absorption at a wavelength of 1.94 microns is the signature of the water molecule due to its vibration mode of excitation. However, since the prior art methods rely on a ratio of that absorption line to a baseline, the measurement is still in error. The software as suggested above that "sees" the entire spectrum in the region of the water signature could simply select another baseline point, or compute the offending signature to re-establish the correct baseline.

Figure 2:
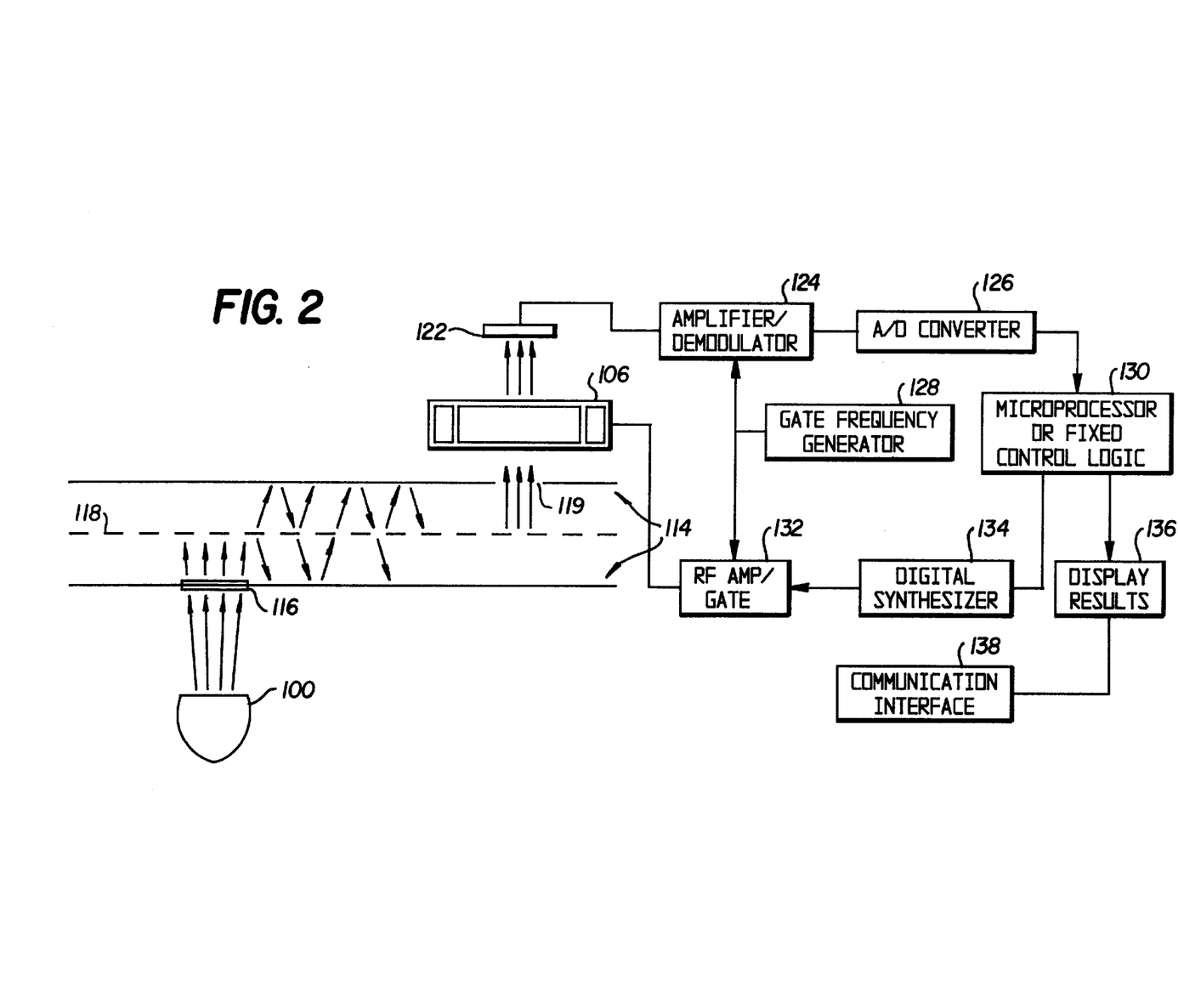
FIG. 2 is a schematic block diagram of an alternate embodiment of the apparatus of the present invention in which the AOTF is utilized to diffract the light exiting from the parallel plate cavity instead of diffracting the light before it enters the parallel reflective plates as shown in the schematic block diagram of FIG. 1.

An alternate embodiment of the instant invention is shown in FIG. 2 in which the quartz-halogen bulb light source 100 is used to launch light of various wavelengths through the inlet opening 116 and directly into the parallel plate cavity device 114. The light exiting from the exit hole 119 impinges upon the AOTF 106 positioned near the exit hole 119. The acousto-optic tunable filter 106 is used to diffract the selected or desired wavelength of light from the light exiting from the exit hole 119 directly into the detector 122. In all other respects, the apparatus shown in FIG. 2 is the same as that shown and described in connection with FIG. 1.

Figure 3:
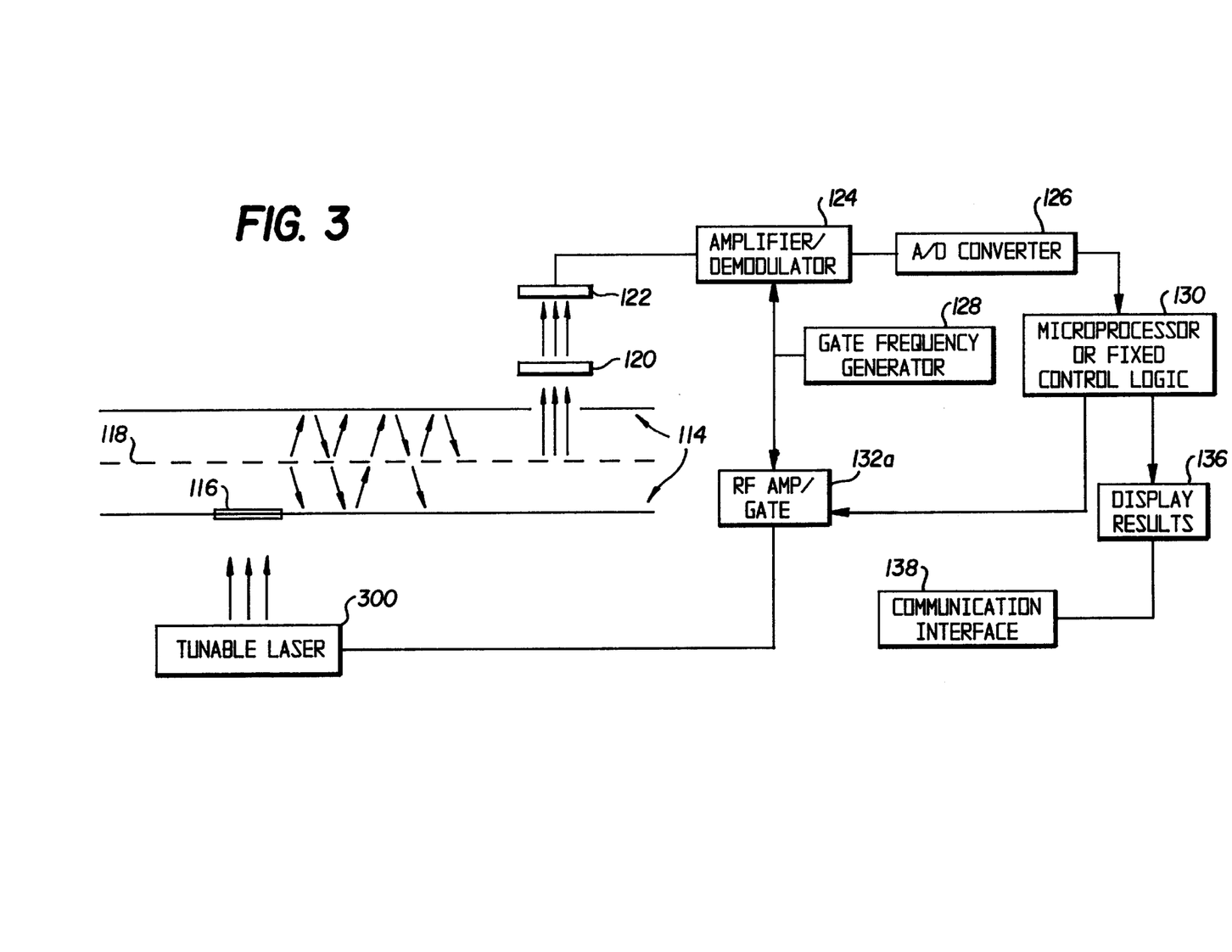
FIG. 3 is a schematic block diagram of another alternative embodiment of the apparatus of the present invention in which a tunable laser light source is utilized to input light into the parallel reflective plates.

Referring now to FIG. 3, there is shown another alternate embodiment of a solid state moisture gauge in which a tunable laser light source 300 is utilized to provide the desired wavelength of light. It is contemplated that the currently available solid-state laser diode light sources which can be made to be tunable, can be utilized as the tunable laser. Alternatively, a conventional tunable laser can also be utilized, but it is more costly than the laser diodes which are currently available. In the embodiment shown in FIG. 3, the tunable laser 300 replaces the radio frequency synthesizer 134, the RF amplifier 132, the acousto-optic tunable filter 106, the light blocking mechanism 108, the lens 104, the heat shield 102 and the quartz-halogen light source 100. The fixed filter 120 may optionally be utilized ahead of the detector 122.

In operation, the output of the microprocessor or fixed control logic 130 commands the tunable laser 300 to the desired wavelength while the gate frequency generator 128 serves to turn the laser on and off, by means of the gate device 132a. Alternatively, the gate frequency generator 128 and gate device 132a can be utilized to modulate the intensity of the tunable laser source 300, for the same purpose of later phase locked detection, all in a known manner. It should be noted, however, that adequate performance can be obtained using simple detection of the light exiting from the exit hole 119 of the parallel plate cavity device 114 and impinging on the detector 122. The use of the phase locked type of detection serves to enhance the signal exiting the amplifier/demodulator 124, as previously described. In all other respects, the solid state moisture gauge shown in FIG. 3 operates in the same manner as discussed in connection with the operation of the solid state moisture gauge of FIG. 1.

Figure 4:
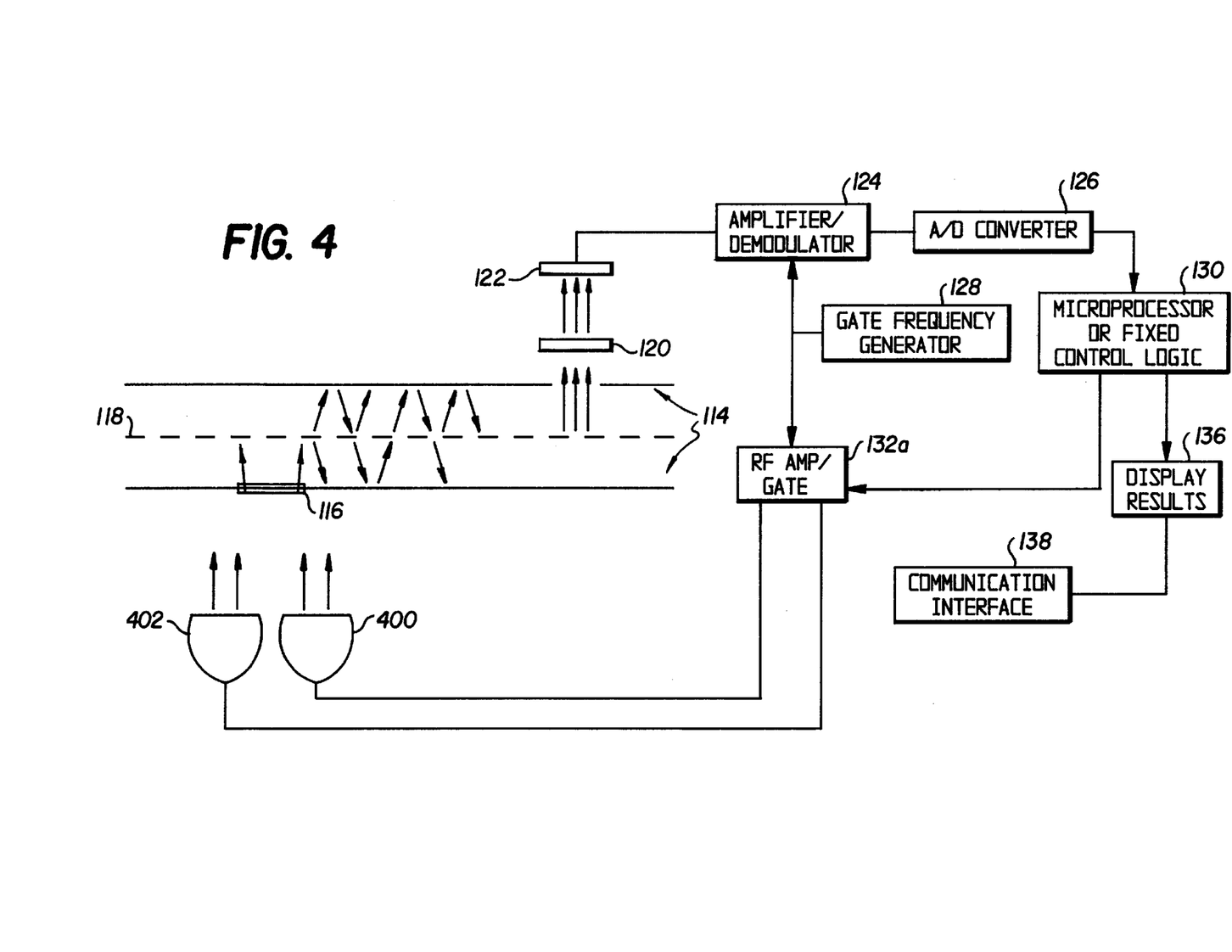
FIG. 4 is a schematic block diagram of yet another alternative embodiment of the apparatus of the present invention in which multiple laser diodes or light emitting diodes are utilized as the light source for the parallel reflective plates.
Figure 5:
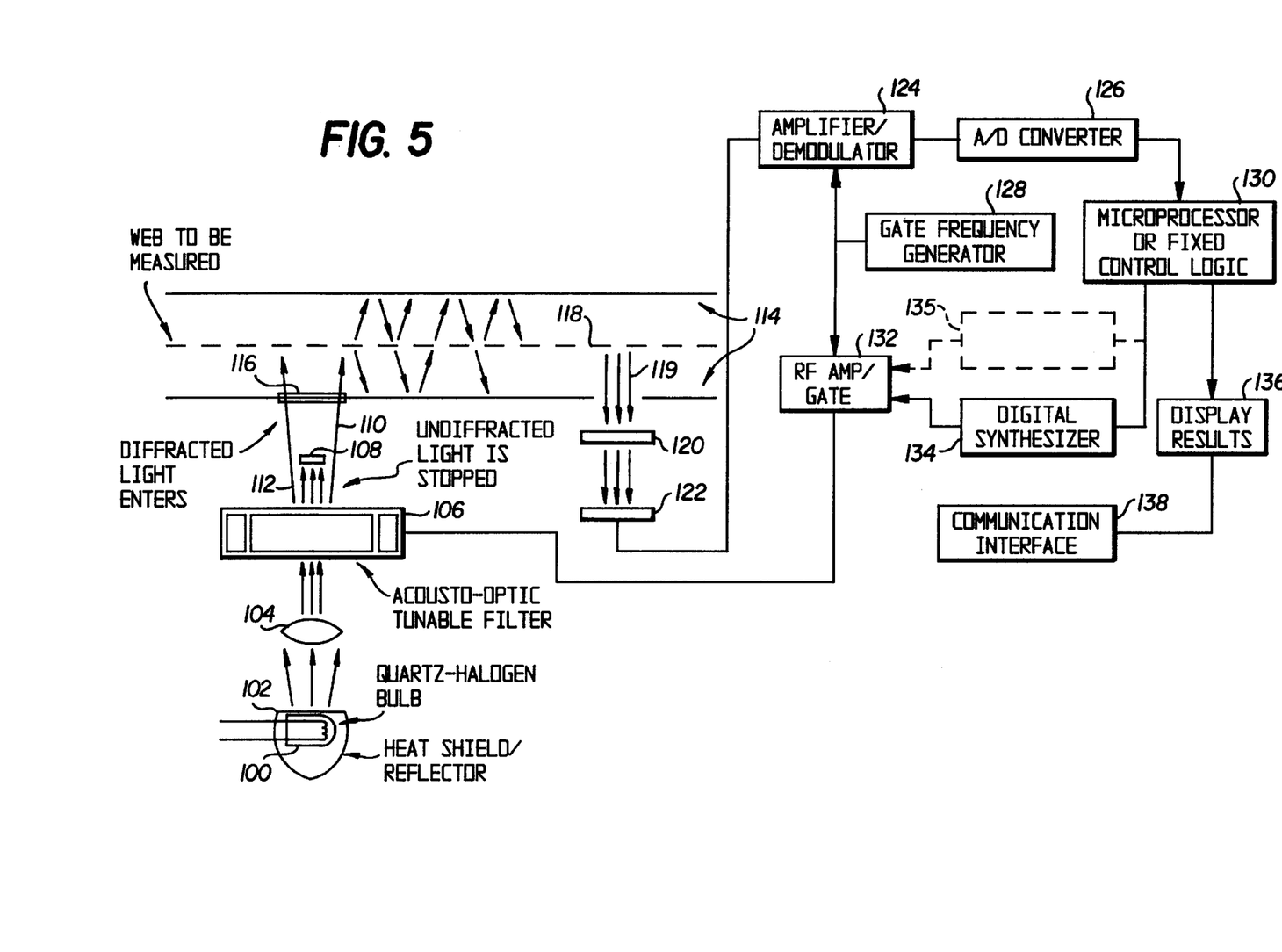
FIG. 5 is schematic block diagram of an alternate embodiment of the apparatus of the present invention of FIG. 1 in which the light enters and exits from the parallel plate cavity on the same side of the cavity.

Still another alternate embodiment of the solid state moisture gauge of the present invention is shown in schematic block diagram form in FIG. 4. As shown in FIG. 4, a different method is used to produce the light which is launched through the entrance hole 116 into the parallel plate cavity device 114. As shown in FIG. 4, one or more light emitting diodes 400, 402 comprised of a mixture of materials that causes them each to emit at a desired wavelength is utilized. These diodes, however, are not tunable. Rather, they are designed to emit at a single desired wavelength. Thus, multiple diodes are used together to create this embodiment of the solid state moisture gauge of the present invention. For example, a first diode 400 that emits light at a wavelength of 1.7 microns and a second diode 402 that emits light at a wavelength of 1.94 microns could be used together to implement the solid state moisture gauge of the present invention shown in FIG. 4. The two diodes 400 and 402 are placed in close proximity to each other and to the entrance hole 116 of the parallel plate cavity device 114 such that their output is coupled into the parallel plate cavity device 114. The two diodes 400 and 402 can be electronically turned on and off, by means of the gate frequency generator 128 and the gate device 132a, one after the other, which would essentially simulate the operation of the acousto-optic tunable filter based solid state moisture gauge shown and described in connection with FIG. 1. Alternatively, both of the diodes 400 and 402 can be turned on together and modulated with different gating frequencies and then phase detected simultaneously, in a manner that could also be implemented with the acousto-optic tunable filter 106.

The acousto-optic tunable filter 106 can alternatively be simultaneously stimulated at multiple radio frequencies, causing multiple wavelengths of light to be diffracted at the same time and launched together into the parallel plate cavity device 114. If each radio frequency source 134, 135 has a different modulating frequency, the various light wavelengths that are produced at the output of the AOTF 106 can be electronically distinguished from one another, after detection by the detector 122, by phase locked detection with the corresponding modulation signal.

A similar scheme can be implemented with multiple light emitting diodes 400 and 402 or with the tunable laser source 300 operated at distinct optical wavelengths. Each diode 400 and 402 can be modulated by an electronic source at a different frequency. Since a diode emits light when it is forward biased, a radio frequency signal is not needed to produce the light, as is the case with the acousto-optic tunable filter 106. The current that forward biases the diodes 400 and 402 is turned on and off or is modulated, at a different frequency, just as the radio frequency source or digital synthesizers 135 and 135 are modulated at different frequencies for use with the acousto-optic tunable filter 106.

The advantage of this aspect of the solid state moisture gauge of the present invention is that the desired wavelengths of light for measuring the moisture content of the material are constantly present and the ratio of the absorption of the light by the material being measured is more certain to be made by light that has passed through the same sample of material for each wavelength. Thus, the potential sources of error in the solid state moisture measurement device are reduced. That is important since, with the various light wavelengths that are generated in a time sequence, as described, for example, in connection with the embodiment shown in FIG. 1, there is the possibility, since the material being measured is typically a moving web, that the light at different wavelengths sees different portions of the material and the common factors of reflection and non-resonant absorption are not in fact common for each wavelength. If that happens, a measurement error results, since the method used to determine moisture based on the ratio of the absorption of the light at the two wavelengths relies on the fact that all other optical interactions for those two wavelengths are the same and that the ratio observed for those two wavelengths is therefore derived from the different absorption of those wavelengths by the presence of water.

When a radio frequency signal causes the acousto-optic tunable filter 106 to diffract a given wavelength of light, the bandwidth or range of wavelengths that are diffracted is rather small. The optical bandwidth is typically about 150 angstroms, or less. Thus, even though the instant application speaks in terms of only one wavelength being diffracted by a given radio frequency source, in reality, a small band of wavelengths is diffracted. That small bandwidth is quite narrow and for most purposes can be considered a single wavelength.

However, since the resonance absorption of the light by the water molecules has a width on the order of 0.15 microns, the bandwidth of 150 angstroms would be only a sliver in the middle of the absorption band. While that generally is an advantage of using acousto-optic tunable filter devices for spectroscopy purposes, when using such devices as a part of the solid state moisture gauge, the bandwidth of the light does not need to be much less than the bandwidth of the absorption resonance.

Thus, while it usually is desirable to strive to narrow emission lineshapes or response curves of instruments, in this instance the narrow lineshape of the light emitted by the typical acousto-optic tunable filter 106 provides no advantages and, in fact, has the effect of reducing the available light energy that is launched into the parallel plate cavity device 114. The result is that the light intensity at the detector 122 is reduced and the signal-to-noise ratio of the measurement is lower than that which could otherwise be achieved.

As is well-known in the art, the theory of acousto-optic tunable filters is that the optical bandwidth of those filters is related to the interaction distance over which the acoustic wave and the light interact. The longer that distance, the larger the crystal which will be required. Therefore, it is desirable to use a smaller crystal in such tunable filter devices which results in a shorter interaction distance. That tends to match the diffraction linewidth resulting from the acousto-optic device to the linewidth of the absorption of the water molecule. Matching those characteristics in that way results in a smaller and more easily integrated acousto-optic device that is also less expensive and requires less radio frequency energy to stimulate in order to produce the desired diffraction. By utilizing a shorter interaction distance, a greater detected light intensity at the detector 122 is achieved.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. An apparatus for measuring an infrared detectable characteristic of a sheet material, said apparatus including means defining a pat for said sheet material and comprising:

a radiation source positioned adjacent to said means defining a path for emitting only diffracted radiation of two different wavelengths directly onto said sheet of material, said radiation source including a light blocking device for preventing undiffracted light generated by said radiation source from impinging to said sheet of material, and said radiation source being electronically controlled to select a desired one of the two different wavelengths being emitted;

a radiation detector adjacent to said means defining a path for receiving a portion of said radiation emitted by said radiation source after said emitted radiation has impinged upon said sheet of material in said means defining a path; and said means defining a path being positioned with respect to said radiation source and detector and said sheet of material such that substantially all of said emitted radiation which impinges on said sheet of material is diffused and reflected by said sheet of material as it travels from said radiation source to said radiation detector, whereby said radiation detector generates electrical signals indicative of the measured infrared detectable characteristic of said sheet of material.

2. The apparatus of claim 1, further including electrical circuitry connected to both said radiation source and said radiation detector for modulating the radiation impinging on said sheet of material and synchronously demodulating said portion of radiation received by said radiation detector.

3. The apparatus of claim 2, further including, an analog-to-digital converter connected to said radiation detector to convert the electrical signals generated by said radiation detector to digital signals; and a digital data processor for receiving and storing said digital signals and for later processing said signals to generate a moisture content value of said sheet of material.

4. The apparatus of claim 1, wherein said radiation source comprises a acousto-optic tunable filter.

5. The apparatus of claim 4, wherein said radiation source is electronically controlled by a digital synthesizer controlled by a digital data processor.

6. The apparatus of claim 1, wherein said infrared detectable characteristic is the moisture content of said sheet of material.

7. The apparatus of claim 1, wherein said radiation source and said radiation detector are spaced apart from each other on the same side of said means defining a path.

8. A method for measuring an infrared detectable characteristic of a sheet of material using apparatus which includes means defining a path for said sheet of material, said method comprising the steps of:

directly impinging at least two different wavelengths of diffracted radiation on said sheet of material by electronically controlling a radiation source positioned adjacent to said means for defining a path to select said at least two different wavelengths of radiation;

blocking undiffracted light generated by said radiation source from impinging on said sheet of material;

detecting at least a portion of each of said at least two different wavelengths of radiation impinging on said sheet of material in said means defining a path using a radiation detector positioned adjacent to said sheet of material but offset from said radiation source;

positioning said means defining a path respect to said radiation source and detector and said sheet of material such that substantially all of said at least two different wavelengths of radiation impinging on said sheet of material is diffused and reflected by said sheet of material as it travels from said radiation source to said radiation detector; and generating electrical signals indicative of the measured infrared detectable characteristic of said sheet of material using said radiation detector.

9. The method of claim 8, wherein each of said at least two different wavelengths of radiation are impinged in turn on said sheet of material.

10. The method of claim 8, further including the steps of modulating said at least two different wavelengths of radiation impinging on said sheet of material and synchronously demodulating said at least two different wavelengths of radiation being detected by said radiation detector.

11. The method of claim 8, wherein said radiation source comprises an acousto-optic tunable filter.

12. The method of claim 11, further including the step of electronically controlling said acousto-optic tunable filter using a digital data processor controlled digital synthesizer.

13. The method of claim 8, further including the step of storing said generated electrical signals in a digital data processor.

14. The method of claim 13, further including the step of converting said generated electrical signals to digital signals prior to storage in said digital data processor.

15. The method of claim 8, wherein said infrared detectable characteristic is the moisture content of said sheet of material.

16. A method for measuring an infrared detectable characteristic of a sheet of material using apparatus which includes means defining a path for said sheet of material, said method comprising the steps of:

directly impinging various wavelengths of diffracted radiation on said sheet of material using an electronically controlled light source positioned adjacent to said means for defining a path;

blocking undiffracted light generated by said radiation source from impinging on said sheet of material;

converting at least a portion of said radiation of various wavelengths impinging on said sheet of material in said means defining a path into at least two different wavelengths of radiation; and detecting said at least two different wavelengths of radiation and generating electrical signals indicative of the measured infrared detectable characteristic of said sheet of material.

17. The method of claim 16, further including the steps of modulating said at least two different wavelengths of radiation during said step of converting and synchronously demodulating said at least two wavelengths of radiation during said step of detecting.

18. The method of claim 16, further including the step of storing said generated electrical signals.

19. The method of claim 18, further including the step of calculating a moisture content value of said sheet of material using said stored electrical signals.

20. The method of claim 16, wherein said step of converting utilizes an acousto-optic tunable filter.

21. The method of claim 16, wherein said converting and detecting steps are controlled by a digital data processor.

22. The method of claim 16, wherein said infrared detectable characteristic is the moisture content of said sheet of material.

* * * * *